United States Patent
Bellhouse et al.

(10) Patent No.: US 7,618,394 B2
(45) Date of Patent: *Nov. 17, 2009

(54) NEEDLELESS SYRINGE USING SUPERSONIC GAS FLOW FOR PARTICLE DELIVERY

(75) Inventors: Brian J. Bellhouse, Islip (GB); David F. Sarphie, Oxford (GB); John C. Greenford, Abingdon (GB)

(73) Assignee: Powderject Research Limited, Oxford (GB)

( * ) Notice: Subject to any disclaimer, the term of this patent is extended or adjusted under 35 U.S.C. 154(b) by 1066 days.

This patent is subject to a terminal disclaimer.

(21) Appl. No.: 10/314,336

(22) Filed: Dec. 9, 2002

(65) Prior Publication Data

US 2005/0165348 A1    Jul. 28, 2005

Related U.S. Application Data (63) Continuation of application No. 09/248,743, filed on Feb. 10, 1999, now Pat. No. 6,881,200, which is a continuation of application No. 08/525,537, filed as application No. PCT/GB94/00753 on Apr. 8, 1994, now abandoned.

(30) Foreign Application Priority Data

| Apr. 8, 1993 | (GB) | ................................. 9307459.9 |
| Sep. 6, 1993 | (GB) | ................................. 9318407.5 |
| Oct. 15, 1993 | (GB) | ................................. 9321356.9 |
| Dec. 21, 1993 | (GB) | ................................. 9326069.3 |

(51) Int. Cl.
    *A61M 5/30*    (2006.01)
(52) U.S. Cl. ...................................... 604/70

(58) Field of Classification Search ................... 604/23, 604/24, 57–59, 68, 70, 72, 131, 140, 146, 604/147, 289, 290, 20, 60, 71, 82, 84, 87–89, 604/91, 85, 86, 119, 416, 232

See application file for complete search history.

(56) References Cited

U.S. PATENT DOCUMENTS

| 2,307,986 A |   | 1/1943  | Bolte et al. |
| 2,605,763 A | * | 8/1952  | Smoot ......................... 604/70 |
| 3,216,562 A |   | 11/1965 | Lockood |
| 3,674,028 A |   | 7/1972  | Ogle |
| 3,736,933 A |   | 6/1973  | Szabo |
| 3,782,380 A |   | 1/1974  | Van Der Gaast |

(Continued)

FOREIGN PATENT DOCUMENTS

DE            170094        12/1904

(Continued)

OTHER PUBLICATIONS

Oard et al, "Transient Gene Expression in Maize, Rice, and Wheat Cells Using an Airgun Apparatus", Plant Physiol (1990) 92, pp. 334-339.

(Continued)

*Primary Examiner*—Manuel A Mendez
(74) *Attorney, Agent, or Firm*—Foley & Lardner LLP (57) ABSTRACT

A needleless syringe having a membrane (28) which is ruptured by gas pressure to generate a supersonic gas flow in which particles containing a therapeutic agent are injected.

43 Claims, 4 Drawing Sheets

U.S. PATENT DOCUMENTS

| | | | | |
|---|---|---|---|---|
| 3,788,315 | A | * | 1/1974 | Laurens .................. 604/70 |
| 3,967,761 | A | | 7/1976 | Melton, Jr. et al. |
| 4,031,892 | A | * | 6/1977 | Hurschman ............. 604/416 |
| 4,069,819 | A | | 1/1978 | Balentini et al. |
| 4,226,236 | A | | 10/1980 | Genese |
| 4,515,586 | A | * | 5/1985 | Mendenhall et al. ....... 604/87 |
| 4,627,432 | A | | 12/1986 | Newell et al. |
| 4,778,054 | A | | 10/1988 | Newell et al. |
| 4,811,731 | A | | 3/1989 | Newell et al. |
| 4,945,050 | A | | 7/1990 | Sanford et al. |
| 4,966,581 | A | | 10/1990 | Landau |
| 5,042,472 | A | | 8/1991 | Bunin |
| 5,046,618 | A | | 9/1991 | Wood |
| 5,053,389 | A | | 10/1991 | Balschmidt et al. |
| 5,064,413 | A | * | 11/1991 | McKinnon et al. ......... 604/70 |
| 5,100,792 | A | | 3/1992 | Sanford et al. |
| 5,120,657 | A | | 6/1992 | McCabe et al. |
| 5,149,655 | A | | 9/1992 | McCabe et al. |
| 5,179,022 | A | | 1/1993 | Sanford et al. |
| 5,204,253 | A | | 4/1993 | Sanford et al. |
| 5,207,217 | A | | 5/1993 | Cocozza et al. |
| 5,239,991 | A | | 8/1993 | Chawla et al. |
| 5,279,608 | A | * | 1/1994 | Cherif Cheikh ......... 604/892.1 |
| 5,349,947 | A | | 9/1994 | Newhouse et al. |
| 5,415,162 | A | | 5/1995 | Casper et al. |
| 5,492,112 | A | | 2/1996 | Mecikalski et al. |
| 5,533,505 | A | | 7/1996 | Kallstrand et al. |
| 5,560,490 | A | | 10/1996 | Chawla et al. |
| 5,575,281 | A | | 11/1996 | Mecikalski |
| 5,584,807 | A | | 12/1996 | McCabe |
| 5,647,349 | A | | 7/1997 | Ohki et al. |
| 5,865,796 | A | | 2/1999 | McCabe |
| 6,881,200 | B2 | * | 4/2005 | Bellhouse et al. ......... 604/68 |

FOREIGN PATENT DOCUMENTS

| | | |
|---|---|---|
| DE | 1 047 385 | 12/1958 |
| EP | 0 313 992 | 5/1989 |
| EP | 0 371 838 | 6/1990 |
| EP | 0 406 778 | 1/1991 |
| EP | 0 458 641 | 11/1991 |
| EP | 0 469 814 | 2/1992 |
| EP | 0 734 737 | 10/1996 |
| FR | 2 360 031 | 12/1978 |
| GB | 501 564 | 3/1939 |
| GB | 677 523 | 8/1952 |
| GB | 1151168 | 5/1969 |
| GB | 2 206 794 | 1/1989 |
| WO | WO 92/04439 | 3/1992 |
| WO | WO 92/10225 | 6/1992 |
| WO | WO 92/12799 | 8/1992 |
| WO | WO 93/03779 | 3/1993 |

OTHER PUBLICATIONS

Rydén et al., "Effect of polymers and microspheres on the nasal absorption of insulin in rats," International Journal of Pharmaceutics, 1992, vol. 83, pp. 1-10.

Williams et al, "Introduction of foreign genes into tissues of living mice by DNA-coated microprojectiles", Genetics (1991), pp. 2726-2730.

* cited by examiner

Fig.3.

NEEDLELESS SYRINGE USING SUPERSONIC GAS FLOW FOR PARTICLE DELIVERY

CROSS-REFERENCE TO RELATED PATENT APPLICATIONS

This application is a Continuation of U.S. patent application Ser. No. 09/248,743, filed Feb. 10, 1999 (issued as U.S. Pat. No. 6,881,200 on Apr. 19, 2005); which is a Continuation of U.S. patent application Ser. No. 08/525,537 filed Sep. 15, 1995 now abandoned (National Stage of PCT/GB94/00753), filed Apr. 8, 1994 (now abandoned).

Previous work has demonstrated the feasibility of using dense carrier particles for the genetic transformation of plant cells. In that biolistic method, dense micro projectiles, made for example of tungsten or gold, are coated with genetic material and fired into target cells. As disclosed in WO-A-92/04439, the micro projectiles were fired by means of an apparatus comprising an elongate tubular device, a pressurizable gas reservoir connected to one end of the device, means between the device ends for holding or introducing particles to be propelled, and a membrane which closes the passage through the tubular device until ruptured on application of a predetermined pressure of gas from the reservoir, whereupon the particles are propelled by the gas flow from the tubular device. As disclosed in the earlier specification, the particles could initially be immobilised, e.g. electrostatically, on or upstream of a rupturable diaphragm, which is ruptured when the gas flow commences, and which may be the same as the rupturable membrane which ruptures to initiate the gas flow. Alternatively it was said that the particles could be injected into the gas stream through a hollow needle.

It is now appreciated that, surprisingly, the earlier technique can be modified to provide a non-invasive drug delivery system by means of a needleless syringe which fires light drug-containing particles in controlled doses into the intact skin.

According to a broad aspect of the invention, a needleless syringe comprises an elongate tubular nozzle, a rupturable membrane initially closing the passage through the nozzle adjacent to the upstream end of the nozzle, particles of a therapeutic agent, particularly a powdered therapeutic agent, located adjacent to the membrane, and energising means for applying to the upstream side of the membrane a gaseous pressure sufficient to burst the membrane and produce through the nozzle a supersonic gas flow in which the particles are entrained.

The syringe may be used for routine delivery of drugs, such as insulin for the treatment of diabetes, and could be of use in mass immunisation programs, or for the delivery of slow-release drugs such as pain killers and contraceptives. The syringe may also be used for the delivery of genetic material into living skin cells, with the long term aim of providing genetic therapy for the stable treatment of diseases such as haemophilia or skin melanoma. The syringe could also be used to deliver genetic material to skin, muscle, blood, lymph and with minor surgery, to organ surfaces.

A delivery system utilising the new syringe reduces the chances of the spread of communicable and auto-immune diseases, which are currently transmitted amongst other means by the re-use of needles. Drug delivery by liquid jet causes skin damage and bleeding and offers no advance over needles in preventing the spread of blood-borne diseases. Thus, the main advantages which flow from the invention include no needle and less pain; no risk of infection; delivery of drugs in natural, solid for; quicker and safer to use than liquid drug, by syringe and needle; and no sharps to dispose of.

Preliminary experiments confirm a theoretical model and establish the efficacy of the new technique, particularly the transdermal injection of powdered drugs. The theoretical model assumes that the skin behaves much like water as a resisting medium. Thus, at low values of Reynolds number the drag follows Stokes law, but at higher values of Reynolds number the drag coefficient is constant. Evidence for this form of drag behaviour on a smooth sphere in a uniform medium, like water, is given in "Mechanics of Fluids" by B S Massey (Van Nostrand). The calculations show that adequate penetration, far example to between 100 and 500 μm beneath the skin is possible using powdered drug particles which are not so large that skin cells will be damaged, utilizing gas velocities e.g. Mach 1-8, preferably Mach 1-3, which are comparatively easily obtainable upon bursting of a rupturable membrane. The penetration depends upon the particle size, that is to say the nominal particle diameter assuming that the particles are roughly spherical, the particle density, the initial velocity upon impacting the skin, and the density and kinematic viscosity of the skin. Different penetration distances will be required depending upon the tissue, e.g. epidermis or muscle, to which the particles are to be delivered for optimum treatment, and the parameters determining penetration will be selected accordingly.

It is a characteristic of the invention that depth of penetration can be closely controlled, thus providing specific administration to a desired locus. Thus, for example, penetration may be chosen at less than 1 mm for an intra-dermally active agent, 1-2 mm for an active agent sub-cutaneously, and 10 mm or more for an agent active when administered intramuscularly. The agent itself will be chosen accordingly. Examples of agents that can be used are viruses or proteins for immunisation, analgesics such as ibuprofen, hormones such as human growth hormone, and drugs such as insulin and calcitonin The agent can be administered without any carrier, diluent or other density-enhancing agent In certain circumstances, e.g. in order to provide a particle of a certain size containing a highly-active drug, some carrier may be present, but the amount will usually be much less than in a conventional pharmaceutical composition, e.g. less than 75% and often less than 50% by volume of the particles. Insulin and calcitonin, for example, will usually be delivered sub-cutaneously. HGH (human growth hormone) may be administered sub-cutaneously or, less frequently, intra-muscularly. The immunogens hepatitis A, meningitis and BCG may be administered intra-muscularly, sub-cutaneously and intra-dermally.

Thus in a first example, insulin particles with a nominal diameter of 10 μm were injected at an initial velocity of 750 m/sec into the skin. Assuming that the insulin particles have a density close to that of the skin, i.e. approximately 1, and that the kinematic viscosity of the skin is assumed to match that of water at $10^{-6}$ m$^2$/sec, the penetration depth before the particles came to rest within the skin is about 200 μm. To obtain greater penetration, the particle size can be increased to 20 μm and the initial velocity to 1,500 m/sec, in which case the penetration depth rises to about 480 μm.

In a second example of the use of the new technique, not for transdermal injection, but for the genetic transformation of cells, for example the injection of DNA-coated tungsten carrier particles into maize cells, a comparable penetration into the tissue would require a reduction in the size of the particles to allow for their increased density. Thus if such coated particles with a nominal diameter of 1 μm, and a density of the order of 20 are injected into maize cells at a velocity of 500 m/sec, the penetration is about 200 μm.

In general, the new injection technique can be carried out with particles having a size of between 0.1 and 250 μm, preferably, for transdermal powdered drug injection, of between 1 and 50 and most preferably between 10 and 20 μma The particles will usually have a density in the range between 0.1 and 25 g/cm$^3$, but for transdermal drug injection, preferably in the range between 0.5 and 2.0 g/cm$^3$, most preferably substantially 1.0 g/cm$^3$. Injection velocities may be between 200 and 2,500 (or even up to 3,000 or more) m/sec, but for transdermal powdered drug injection, preferably between 500 and 1,500 and most preferably between 750 and 1,000 m/sec.

The powdered therapeutic agent will normally be ground and sieved to a precise diameter. Alternatively the particles could be tiny spherical shells of for example, up to 100 μm diameter, in which solid or liquid drugs are encapsulated. If the encapsulating shell has a controlled permeability, this may provide an additional means of providing a slow drug release rate after delivery. A substantially inert carrier may have to be included to provide the particles with the required size and mass for adequate penetration, particularly if the therapeutic agent is potent or of low density. The carrier may be mixed with the agent, or provide the encapsulating shells. The required dose will depend on the quantity and concentration of the agent and the number of particles in a shot.

A different approach in setting acceptable operating parameters for the new technique is to select the particle size, mass and initial velocity to give a momentum density, that is particle momentum divided by particle frontal area, of between 2 and 10, preferably between 4 and 7 kg/sec/m. Control of momentum density is desirable, in order to achieve controlled, tissue-selective administration. In the first example mentioned above, in which powdered insulin with a particle size of 10 μm is fired at a velocity of 750 m/sec, the momentum density is 5 kg/sec/m. In the second example involving the injection of DNA-coated tungsten carrier particles into maize cells, the particles having a nominal diameter of 1 μm and a velocity of 500 m/sec, the momentum density is 6-7 kg/sec/m. The invention also includes a needleless syringe, for therapeutic use, which comprises a nozzle, particles of a powdered therapeutic agent, and energising means which, on activation, deliver the particles through the nozzle at a velocity of at least 200, preferably in the range of between 200 and 2,500, m/sec, in which the particles have a size predominantly in the range 0.1 to 250 μm and a density in the range of 0.1 to 25 g/cm$^3$, and in which the agent comprises a drug having the therapeutic use and, preferably, no, or a minor amount (i.e. <50%) by volume of, inert carrier or diluent.

Further the invention includes a method of therapeutic treatment, comprising the transdermal delivery of particles of a powdered therapeutic agent, which comprises administering the particles to the locus of transdermal administration at a velocity of at least 200, preferably in the range of between 200 and 2,500, m/sec, in which the particles have a size predominantly in the range 0.1 to 250 μm and a density in the range of 0.1 to 25 g/cm$^3$, and in which the agent comprises a drug having the therapeutic use and, preferably, no, or a minor amount (i.e. <50%) by volume of, inert carrier or diluent.

With regard to the construction of the syringe, the energising means may comprise a chamber upstream of the membrane, and conveniently in a handle of the syringe, and means for the controlled build up of gaseous pressure in the chamber, in which case the means for building up the pressure in the chamber may comprise a source of compressed gas connected to the chamber through e.g. a fast coupling and a bleed valve. Alternatively, the syringe His self-contained and portable and incorporates its own reservoir of compressed gas, which may be rechargeable.

Typical operating values for a practical system are a burst pressure of the diaphragms of between 20 and 75 atmospheres in a pressure chamber having a volume of between 1 and 5 ml, generating a supersonic shockwave at velocities of between Mach 1 and Mach 8, preferably between Mach 1 and Mach 3.

The gas/particle velocity leaving the nozzle and hence penetration depth is dependent an membrane burst pressure but, surprisingly for such a transient phenomenon, experiments have shown that the velocity is also critically dependent on nozzle geometry, This is useful as it enables the penetration depth to be controlled by changing the nozzle rather than the membrane thickness. The nozzle preferably has a convergent upstream portion leading through a throat to a cylindrical or, preferably, divergent downstream portion. The upstream portion allows the sealed unit of agent to be accommodated in a wider portion and the supersonic shock wave is produced at the that. The divergence of the downstream portion significantly affects the velocity of the gas being expanded to pseudo-steady-state, supersonic velocities. Increases in this pseudo-steady-state velocity results in increased particle depth of penetration which is surprising for a phenomenon considered to be predominantly transient. The divergent portion also appears to transform the transient flow pattern upon bursting of the membrane into a smooth exit flow from the nozzle, thereby rendering uniform the travel of the particles into their target. In addition the divergence of the nozzle causes an even spread of the particles onto the target.

In one series of experiments utilising helium upstream of the membrane, and varying only the membrane burst pressure, penetration into a uniform target was measured. Burst pressures of 42,61 and 100 atmospheres produced penetration depths of 38,50 and 70 units respectively. In contrast, similar experiments in which only the internal geometry of the divergent portion of the nozzle was changed also produced different penetration. Thus three nozzles of the same length and exit diameter but different internal geometries chosen to produce Mach numbers of 1, 2 and 3 under theoretical steady state conditions produced target penetration depths of 15, 21 and 34 units respectively.

The type of gas used for the delivery is not, prima facie, critical and comparatively cheap gases such as helium, nitrogen and carbon dioxide are appropriate. However, the gas applied to the upstream side of the membrane to rupture the membrane should be sterile as it will contribute to the gas flow carrying the particles through the nozzle to the patient's skin or other target. For this purpose helium is useful as it is available in inert, sterile form.

It has now been appreciated that there is another advantage in using helium for bursting the membrane. It is believed that most of the particles travel on the contact surface between the upstream and downstream gases which are initially separated by the membrane, the contact surface closely following the shockwave. It appears that the lighter the gas applied to the upstream side of the membrane, the greater the shockwave (and contact surface) velocity through the nozzle for a given pressure differential across the membrane at the time of rupture and a given nozzle geometry. It follows that if a light gas is used the required shockwave velocity can be achieved with a lower pressure differential, provided that the membrane will rupture at that pressure differential. In general therefore the gas applied to the upstream side of the membrane to burst the membrane is lighter than air.

This appreciation has lead to a further understanding that the velocity of the shockwave through the nozzle is greater, the lighter the gas within the nozzle. It has been suggested to use at least a partial vacuum but this is difficult to provide and maintain in practice. In order therefore to further minimise the required burst pressure of the membrane to achieve a required shockwave (and contact surface) velocity in the nozzle, the interior of the nozzle downstream of the membrane preferably contains a gas, such as helium, which is lighter than air, at substantially atmospheric pressure, the light gas being contained by a readily removable seal, such as a removable plug or cap, or a peelable foil, at the downstream end of the nozzle. In use the seal will be removed immediately before operation of the syringe, so that the light gas will have little time to diffuse out of the nozzle before the syringe is fired.

The sealing of the downstream end of the nozzle also has the additional advantage that it remains sterile so that there is minimum chance of any foreign bodies entering the nozzle, after, far example, undoing a sterile package, and before firing the syringe, as such foreign bodies would inevitably be entrained by the gas flow carrying the drug particles to the patient's skin or other target.

The particle source should contain a precise dose of the drug and be capable of being handled as a sterile assembly. Indeed, absolute sterility is sought and consequently it is to be assumed that at least the assembly of tubular nozzle, and remnants of the particle source and burst membrane, and possibly also the pressurizable chamber, will be disposable for replacement by a new assembly from a sealed sterile package. It is quite possible that the entire device, including energising mechanism, pressurizable chamber, nozzle, membrane and particles will be for a single use and that all the remnants of the device will be disposable after use. This disposable assembly would naturally be made as cheaply as possible, particularly from plastic material. Alternatively, the syringe may readily be separable into two parts: a disposable downstream part comprising at least the sterile nozzle, membrane and particles, and an upstream part comprising at least part of the energising means However in this particular configuration, the source of pressurized gas and its coupling to the pressurizable chamber would not be disposable, being comparatively expensive metal parts. Because exposed end and interior surfaces of these parts will come into communication with the interior of the pressurizable chamber, and hence during drug delivery with the interior of the tubular nozzle, there is a danger of contamination from bacteria and other contaminants settling on the nondisposable parts.

Preferably therefore the upstream end of the chamber is closed by a sterile harrier, such as a semi-permeable membrane which allows the passage of gas but not of bacteria therethrough. Alternatively, the chamber may be cylindrical and the sterile barrier is a piston, there being means for advancing the piston in the cylindrical chamber to compress the gas therein. The means for advancing the piston may be a source of compressed gas applied to the upstream end of the piston. The syringe may then be self-contained and portable, and incorporates its own reservoir of compressed gas, and a valve which can be opened manually to expose the piston to the gas pressure. Alternatively the means for advancing the piston comprises a spring which is arranged to be stressed and then released manually to advance the piston.

The provision of the piston ensures that there is initially a predetermined volume of gas at a predetermined pressure which may be increased by moving the piston along within the cylindrical chamber, however slowly, until the pressure in the chamber is sufficient to burst the membrane and deliver the particles. The amount of gas which flows through the tubular device is therefore precisely predetermined, and produces little objectionable noise. The swept volume of the cylinder necessary to increase the gas pressure to, say, between 20 and 40 bar, sufficient to burst the membrane, may be minimised if the helium or other gas in the cylindrical chamber is prepressurized to a super atmospheric pressure of, say, 2 bar prior to advance of the piston. Also, in order to avoid a dead space between the leading end of the piston and the membrane, when it bulges away from the piston immediately before bursting, the nose of the piston is preferably convex so as to be capable of approaching the centre of the membrane more closely.

When the syringe is to be used clinically for drug delivery, it is expected that the assembly of tubular nozzle, membrane, particles, cylindrical chamber, energising means and piston will be supplied in a sealed sterile package and be disposable after use. In the alternative arrangement comprising disposable and non-disposable parts, contamination from the means far moving the piston, whether it be a spring, a manual plunger or a source of pressurized fluid behind the piston, will be avoided because the piston maintains, throughout the drug delivery, a barrier isolating the nondisposable parts upstream of the piston from the interior of the disposable parts downstream of the piston.

The disposable assembly will, naturally, be manufactured as cheaply as possible, particularly from plastic material. Since, during delivery, a high pressure will build up in the cylindrical chamber, tending to enlarge the wall of the chamber outwardly, with a danger of back leakage of gas past the piston, the wall of the cylindrical chamber may be made of a rigid engineering plastic material. Alternatively, and more cheaply, the cylindrical chamber may, in use, be contained within a rigid casing, in which it is a close fit. This casing need not be disposable.

Another use for the new syringe is in the laboratory for the delivery of genetic material into living cells for genetic transformation. In that event, assuming comparatively sterile conditions within the laboratory, it may not be necessary for disposable parts to be preassembled in a sterile condition, it may be sufficient for the syringe to be assembled in the laboratory, for example from components including a separate (possibly disposable) tubular nozzle and cylindrical chamber component, which are separable to allow the replacement of a ruptured membrane, and a separate piston component to be inserted into the cylindrical chamber aster genetic material has been dosed onto the membrane.

The various means disclosed in WO-A-92/04439 for locating the particles prior to rupture of the membrane are suitable when the particles are made from a very dense metal and/or for the genetic transformation of plant cells in which case it is not critical as to how many of the particles reach the target. However, the earlier apparatus is not suitable for powdered drugs because the drug-containing particles are so light that they are difficult to immobilise prior to propulsion, must be deliverable in the prescribed dose, and maintained sterile prior to delivery. For this purpose, the particles of powdered therapeutic agent are preferably located between two rupturable diaphragms extending across the interior of the nozzle.

One of the two diaphragms, or indeed both, may form the main rupturable membrane, the rupture of which initiates the gas flow. Alternatively, the unit may be located upstream or downstream of the main rupturable membrane, at any convenient position along the nozzle.

The membrane and diaphragm or diaphragms, may be permanent fixtures in a disposable syringe or disposable part of the syringe, or they may be clamped at their edges between connectable parts of the nozzle, for example between screwed together sections.

Preferably the edges of the diaphragms are sealed together directly around their edges to form a common sachet or capsule containing the particles, or indirectly, for example by being sealed to opposite axial faces of an intervening ring. In either case the edges of the sealed unit may be gripped between separable portions of the nozzle.

The sachet, capsule, or other sealed unit, may include three or more of the diaphragms to provide multiple isolated components containing different powdered therapeutic agents to be injected together. This would be useful for the delivery of mixtures of drugs which might otherwise react unfavourably even when dry. The unit may be handled as a sterile assembly and contains a precise dose of the drug. By arranging for it to burst when the membrane bursts, it can be ensured that the drug is available at the right dosage and when needed. A particular advantage of the new technique of injecting dry powdered drugs is that it can be used for delivering a stable mixture of drugs, which are unstable when mixed wet. The invention includes such a stable mixture of powdered drugs for use in a syringe according to the invention.

The sealed unit contains a predetermined dose of drug and it is important that substantially the whole of this dose is delivered to the patient's skin. It is therefore important that virtually none of the particles remain trapped between the diaphragms adjacent to their edges after rupture. For this reason, at least one of the diaphragms is preferably dimpled away from the other to provide a separation sufficient to locate the majority of the particles radially inwardly of the diaphragm edges.

The invention also includes a product for therapeutic use, comprising a sealed unit of or for the new syringe, the unit comprising two diaphragms which are directly or indirectly sealed to one another around their edges, and which contain particles of a powdered therapeutic agent for transdermal injection.

It might be expected that the closer the nozzle to the patient's skin, the greater the depth of particle penetration. While that is true as the spacing is reduced from a distance of some tens of mm, experiments show that there is an optimum spacing for maximum penetration and that this reduces sharply with further approach of the nozzle to the skin, probably because of the reflected shock wave interfering with the contact surface.

It may therefore be desirable to provide, a spacer at the downstream, outlet end of the nozzle to provide a positive spacing of the nozzle from the patient's skin of up to 35 mm, preferably between 5 and 15 mm. A further desirability of providing this spacing between the nozzle and patient's skin is to enable the jet leaving the nozzle to expand radially outwardly and consequently to cause the particles to impinge on a much larger area of the patient's skin than the cross-sectional area of the nozzle. For example, if the nozzle has, at its downstream end, an outlet opening of about 2.5 m in diameter, a desirable divergence of the jet would cause it to impinge substantially uniformly on an area of the patient's skin of the order of 20-30 mm in diameter. Consequently, it is preferred if the spacer is a tubular shroud sufficiently large and shaped so that it does not prevent a jet of gas-entrained drug-containing particles leaving the nozzle outlet, in use, from expanding to a cross-section at least five and preferably at least ten times the area of the outlet at a position level with the downstream end of the shroud, that is where the shroud when in use will be pressed against the patient's skin.

The spacer may be associated with a silencer or sound attenuating medium such as cotton wool. A perforate spacer may provide an adequate silencing effect. Preferably, the tubular shroud providing the spacer is imperforate and a silencer is positioned in an annular space within a barrel surrounding the nozzle to receive the shockwave reflected from the patient's skin back through the spacer shroud. The silencer may be of labyrinthine construction and provide e.g., a tortuous path between interdigitating annular flanges extending radially outwardly from the surface of the nozzle and radially inwardly from the barrel, the path leading to at least one outlet to the atmosphere through the wall of the barrel. This has been found to be remarkably efficient in reducing the otherwise frightening noise which is created when the diaphragm is burst and the shockwave leaves the nozzle to carry the particles into contact with the patient's skin.

The following Example illustrates the utility of a needle-less syringe of the invention.

EXAMPLE

Figure 1:
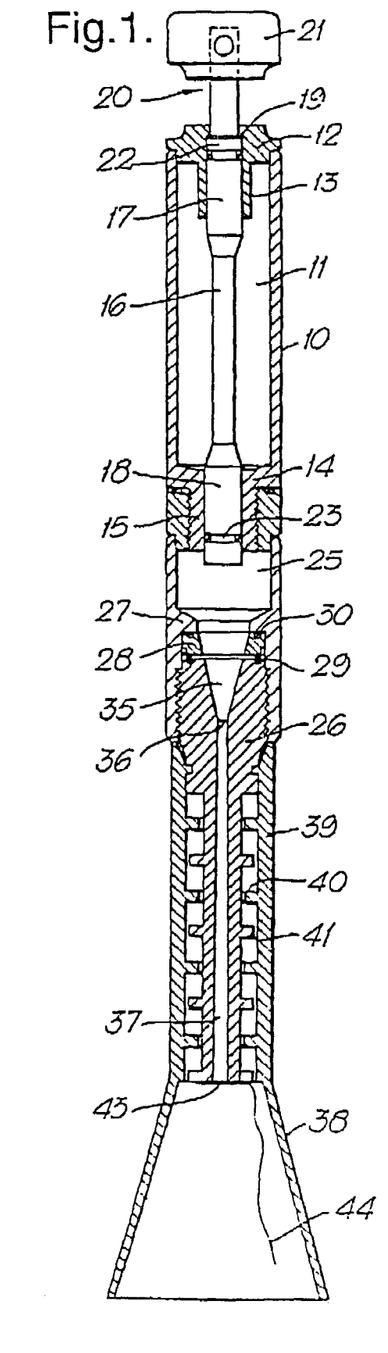
FIG. 1 is a axial section through a first example.

Eight healthy, male, albino rats (Wistar, avg. mass: 250 g) were anaesthetized with injections of 0.25 ml Sagatal (sodium penthathol barbitone, 60 mg/ml). The fur in the peritoneal region of each was removed using a commercially-available depilatory creme (Immac) Animals 1 to 4 were then injected with 0.1 mg bovine insulin (powder form, Sigma) using a needle-less syringe as illustrated in FIG. 1 of the accompanying drawings. Animals 5 and 6 were injected with 1 mg bovine insulin (powder form) under identical conditions. The average insulin particle size was c. 10 μm, and the delivery velocity 750 m/s. For comparison, animals 7 and 8 were injected with 0.1 mg insulin dissolved in 0.9% aqueous NaCl, using a conventional syringe, via a needle.

Blood samples from each of the experimental animals were taken prior to injection (to act as control) and then at four hours post-injection. In each case, 3 drops of blood (approximately 50 μl) were removed from the tail of the animal and mixed with 2 μl heparin, to prevent clotting. This mixture was then mixed with 100 μl of 6% perchloric acid, to halt glucose metabolism. The mixture was then spun and the supernatant assayed for blood glucose.

Blood glucose levels (BGL) for animals 1 to 6 are given in the following table:

| Animal | ELG (mM) | |
| --- | --- | --- |
| | 0 Hr | 4 Hr |
| 1 | 5.30 | 2.22 |
| 2 | 5.40 | 1.29 |
| 3 | 7.22 | 1.51 |
| 4 | 5.64 | 2.87 |
| 5 | 5.07 | 0.91 |
| 6 | 5.36 | 2.63 |

Results from animals 7 and 8 showed BGL values of 2.2-3.3 mM and 2.0-2.4 mM after 1 and 2 hours, respectively. From these results, it is apparent that insulin has been delivered by needle-less injection in sufficient quantities to produce a significant therapeutic effect, and that the level of this therapeutic effect appears to be comparable to that resulting from conventional needle/syringe injection. Comparison of these results at four hours with other results show that reduction in operating pressure (from 65 bar to 40 bar) and the reduction in insulin "payload" (from 1.0 mg to 0.1 mg) produce no significant differences in BGL. This is extremely important for three reasons:

i) reduced operating pressure reduces structural requirements for the eventual design of mass-produced clinical devices;
ii) reduced operating pressure ensures the elimination of any adverse effects which might occur at the target skin; and
iii) reduced drug payload demonstrates that this method of delivery is highly efficient, ensuring that the bio-availability associated with this delivery technique will be sufficient.

Some examples of syringes constructed in accordance with the present invention are illustrated in the accompanying drawings, in which.

Figure 2:
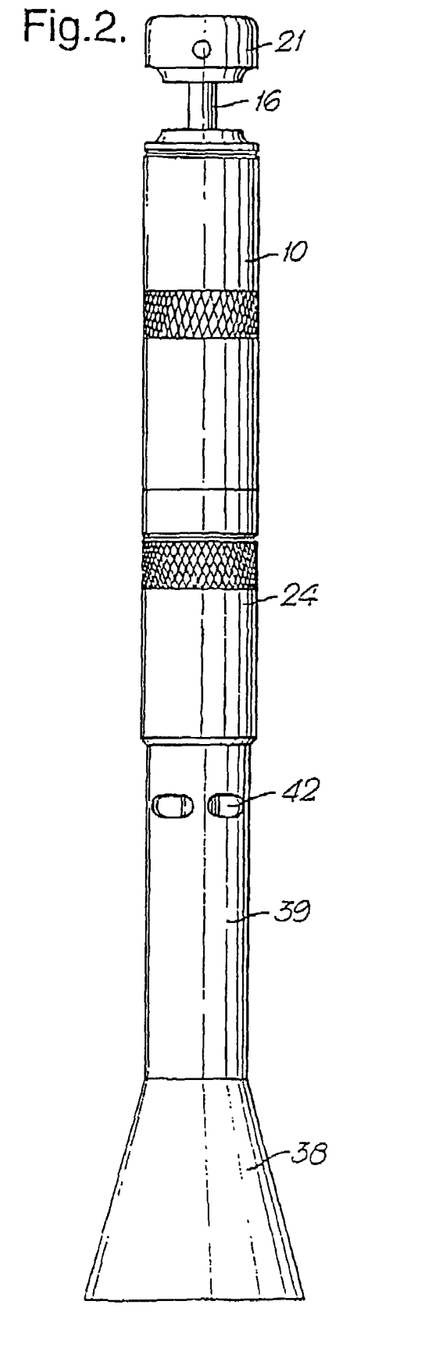
FIG. 2 is an elevation of the first example.
Figure 3:
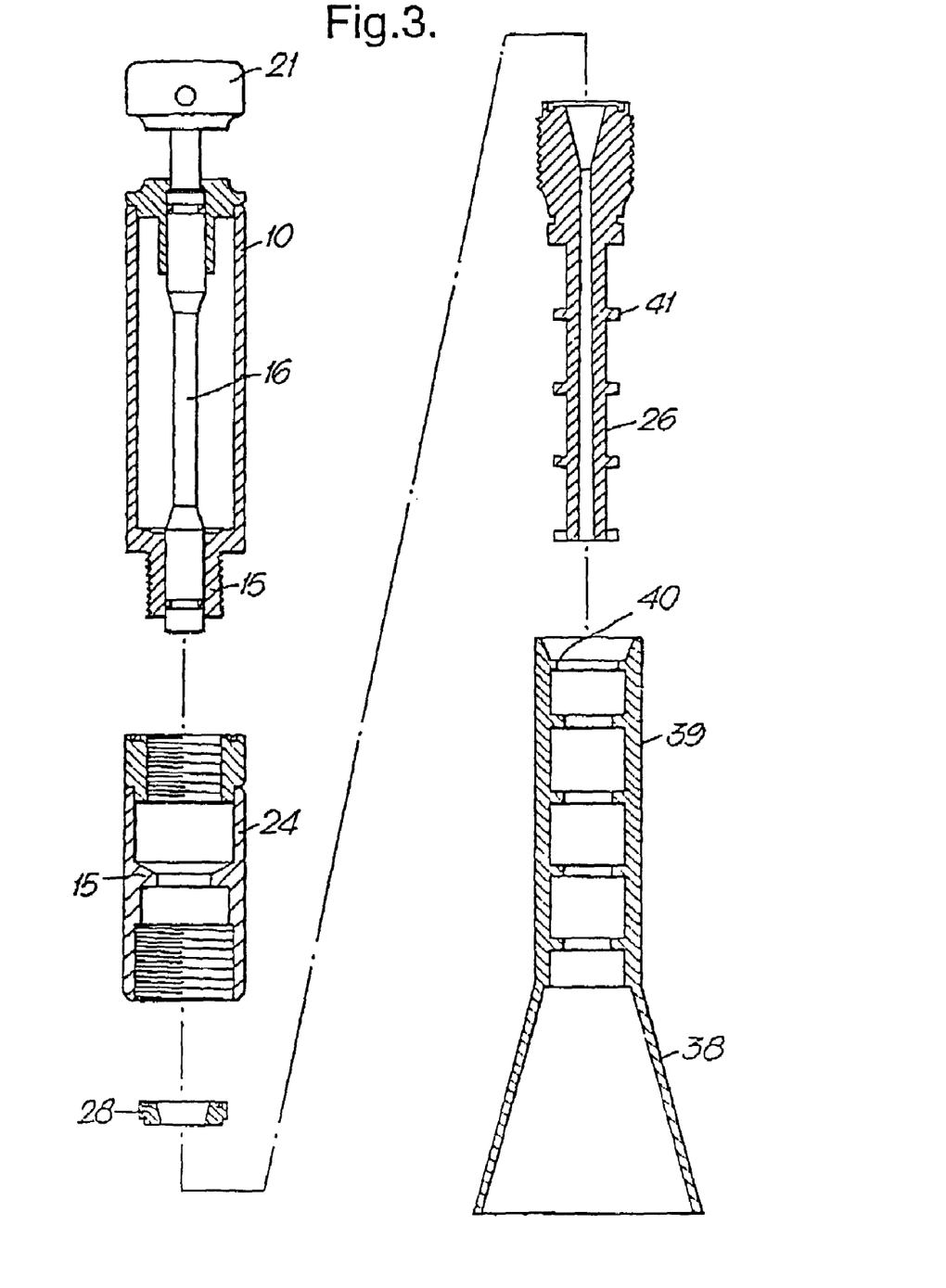
FIG. 3 is an exploded version of FIG. 1.

The first syringe illustrated in FIGS. 1 to 3 is some 18 cm long and arranged to be held in the palm of the hand with the thumb overlying the upper end. It comprises an upper cylindrical barrel portion 10 containing a reservoir 11. The upper end of the barrel portion 10 is closed by an end plug 12, having a depending skirt 13. The lower end of the barrel portion 10 is closed by an integral end wall 14 formed with a depending externally screw threaded skirt 15. A plunger 16 has upper and lower cylindrical enlargements 17 and 18, which slide within the skirts 13 and 15 respectively. Upward movement of the slider is limited by abutment of the upper end of the enlargement 17 with a shoulder 19 in the end cap 12. The plunger can be moved downwardly from this position through a stroke equivalent to the gap 20 shown in FIG. 1 by downward pressure on a button 21 fixed to the upper end of the plunger 16. Throughout this stroke the enlargement 17 remains sealed to the skirt 13 by means of an O-ring 22. In the raised position of the plunger, the enlargement 18 is sealed to the skirt 15 by means of an O-ring 23, to seal the reservoir 11, but when the plunger is forced downwardly, the seal exits the lower end of the skirt 15 to provide an outlet from the reservoir 11 in a clearance between the enlargement 19 and the skirt 15.

Screwed to the bottom of the upper barrel portion 10 is a lower cylindrical barrel portion 24 containing a pressure chamber 25. Screwed into the lower end of the barrel portion 24 is a nozzle 26. Secured and sealed between the upper end of the nozzle 26 and the under side of an annular rib 27, formed integrally with the barrel portion 24, is a capsule 28 containing particles to be injected. The capsule is sealed to the nozzle 26 and rib 27 by O-rings 29 and 30, recessed in the nozzle and capsule respectively.

Figure 8:
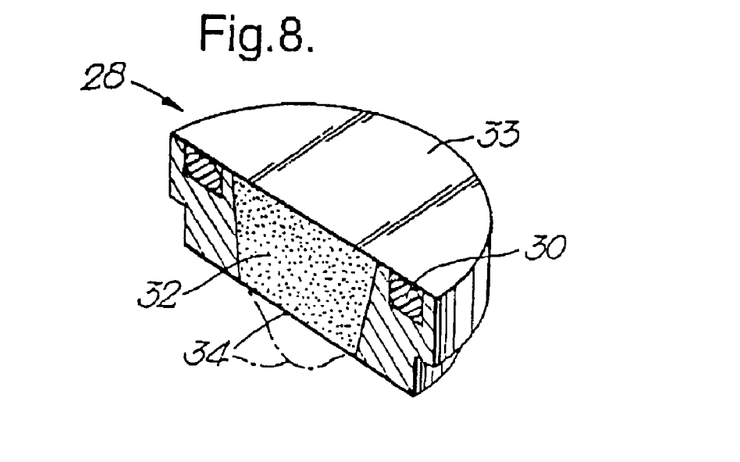

As shown in FIG. 8, the capsule comprises an annular ring 31, having a frustoconical internal periphery surrounding a compartment 32, containing the particles to be injected. The top of the compartment is closed by a comparatively weak Mylar diaphragm 33 and at the bottom by a stronger Mylar diaphragm 34. These diaphragms may be sealed to the upper and lower walls of the ring 31 by the compression between the nozzle 26 and rib 27, but are preferably heat or otherwise bonded to the faces of the ring, so that the capsule norms a self-contained sealed unit. The diaphragm 34 may be dimpled downwardly as shown in dotted lines, to assist in ensuring that all the particles are carried from the compartment when the diaphragms burst in use. The ring may be split into two parts with a third, weak, diaphragm between the parts so as to provide two separate compartments.

The passageway through the nozzle 25 has an upper convergent (in the downward direction of flow) part 35 leading through a throat 36 to a divergent part 37. The convergent portion is a continuation of the frustoconical internal shape of the ring 31. The nozzle is surrounded by a tubular portion providing a divergent spacer shroud 38 and a cylindrical silencer part 39 made in two halves divided by a longitudinal diametral plane. The upper ends of these two halves are received on a cylindrical surface 40 of the nozzle where they are retained in position by the inter-engagement of an annular rib and groove 41. The two halves are then bonded together. The inner surface of the cylindrical part 39 is integrally formed with a number of axially spaced, radially inwardly projecting flanges 40. The outer surface of the nozzle is complementarily provided with a series of radially outwardly extending flanges 41, each axially spaced equidistant between a respective adjacent pair of the flanges 40. The outer diameter of the flanges 41 is very slightly greater than the inner diameter of the flanges 40. A ring of exhaust outlets 42 is formed in the cylindrical part 39, adjacent to its upper end.

It is intended that the barrel portion 10 will be reusable, and will be made of metal or plastics material. It is intended that the parts screwed to the bottom of the barrel portion 10 will be made primarily of plastics material and will be disposable after a single use. In an alternative embodiment, the entire device will be made of a plastics material, will be provided in sterile packaging and will be disposable after a single use.

In use the reservoir 11 in the barrel portion 10 is charged with a gas, such as helium under pressure, by screwing a supply conduit onto the skirt 15, and depressing the plunger 16 so that the reservoir is charged by flow upwards around the enlargement 18. When the button 21 is released, the plunger 16 will be retracted to seal the reservoir 11 by the supply pressure acting on the underside of the enlargement 18.

The remaining part of the syringe will normally be supplied in a sealed sterile packet with the capsule 28 in place, and with the passageway through the nozzle 26 filled with a light gas such as helium, at substantially atmospheric pressure, and contained by a foil 43 removably secured by adhesive to the bottom face of the nozzle, and having a tab 44. This part is screwed to the barrel portion 10.

In order to carry out an injection, the wider end of the spacer shroud 38 is pressed against a patient's skin and, after first removing the foil 43 by pulling on the tab 44, the button 21 is depressed. The gas released from the reservoir 11 into the chamber 25 eventually creates in the chamber a pressure sufficient to burst the diaphragms 33 and 34 and allow the gas to travel through the nozzle 26, with the particles entrained thereby into the patient's skin. The shockwave reflected from the patient's skin travels up through the labyrinthine passageway between the nozzle 26 and surrounding cylindrical portion 39, through the tortuous path between the flanges 40 and 41, and eventually out through the opening 42, acting as a silencer and attenuating the noise of the gas discharge.

A charge of gas in the reservoir 11 could be sufficient for five or ten injections, although the current prototype only allows for a single injection, before it is necessary for the reservoir to be recharged. After the injection, it will be normal for at least the disposable parts attached to the bottom of the barrel portion 10 to be disposed of. However, it is conceivable that in certain situations, the nozzle could be unscrewed from the lower barrel portion 24, and a new capsule 26 fitted prior to a new injection being carried out. If the reservoir is to contain enough gas for multiple injections, the plunger 16 will preferably be spring-loaded upwards so that the lower end of the reservoir is reclosed upon release of the button 21 as soon as the syringe has been fired.

Figure 4:
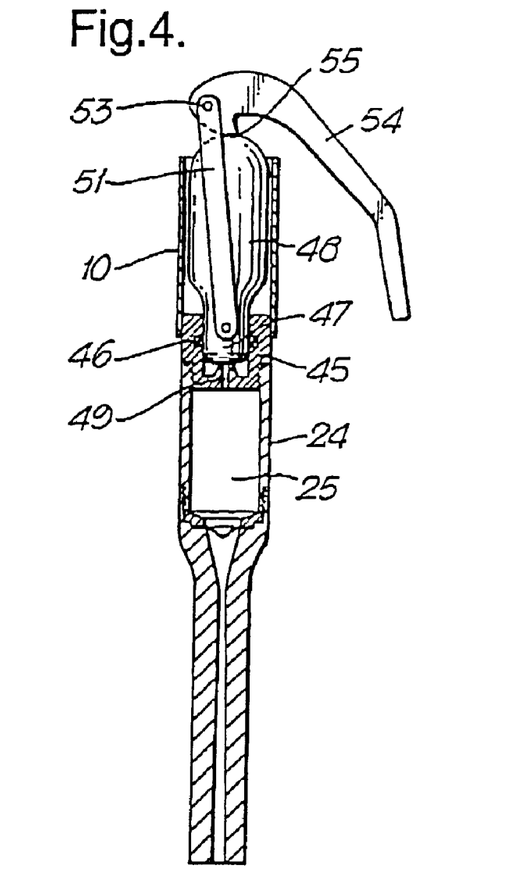
FIGS. 4, 5 and 6 are sections similar to FIG. 1 but of second, third and fourth examples, respectively.

FIG. 4 shows a modification in which the upper barrel portion 10 has an open upper end, and is secured at its lower end to a coupling 45 which is screwed to the upper end of a lower barrel portion 24. The coupling has a socket with an O-ring 46 for receiving and sealing within the socket a neck 47 on a metal bulb 48, containing a pressurized gas such as helium, which is loosely received within the barrel portion 10. The bottom wall of the coupling 45 is provided with an upstanding projection 49 through which there passes a passageway 50 opening into the chamber 25. A pair of arms 51, extending down opposite sides of the barrel portion 10, are pivoted at 52, adjacent to their lower ends, to the barrel portion 10, and at 53, adjacent to their upper ends, to a lever 54, having a cam nose 95 arranged to engage the upper end of the bulb 48. The neck 47 of the bulb contains a spring loaded valve which is opened upon inward pressure into the neck by the hollow projection 49 when the lever 54 is rotated clockwise as seen in FIG. 4 to force the bulb 48 further into the socket 45.

The parts below the chamber 25 are only shown diagrammatically in FIG. 4 but may include all the features, such as the spacer/silencer and foil seal, shown in FIGS. 1 to 3. Operation is analogous to the first example in that when the chamber 25 is to be pressurized for an injection, the lever 54 is operated to release gas from the bulb 48 into the chamber 25. In this case some or all of the parts may be disposable after each injection.

In the first two examples, a semi-permeable membrane, which filters out any bacteria or foreign matter in the gas supply, may be fixed at its edges to the barrel portion 24, e.g. between two parts of the portion 24, which are connected by a screw threader connection, and extend across the interior of the portion 24, upstream of the capsule 28

Figure 5:
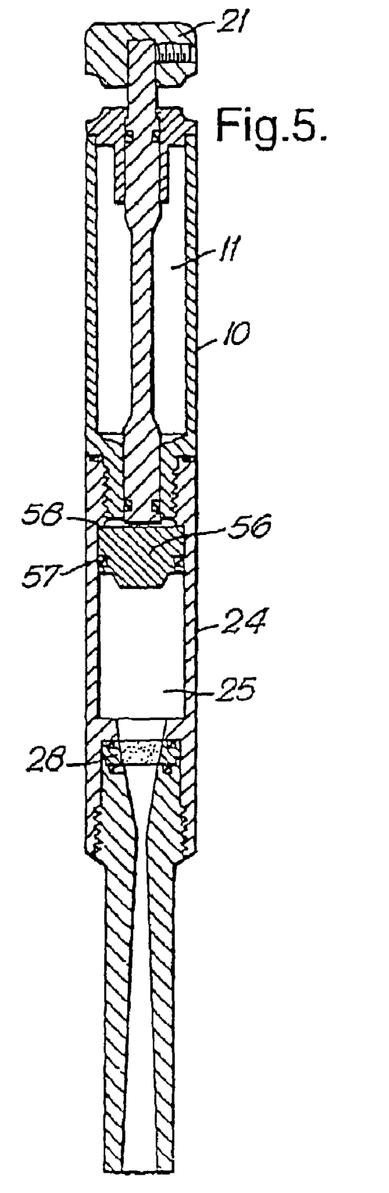

FIG. 5 shows a modification of the first example and although not shown, the spacer silencer and foil may be provided as in the first example. The essential difference is that the barrel portion 24 is longer and is provided with a piston 56, which is sealed to the inner wall of the barrel portion 24 by an O-ring 57. The piston is captive in the barrel portion 24 by engagement with an annular shoulder 58.

In this case the chamber 25 may be prefilled with gas, such as helium, at a superatmospheric pressure of, say, 2-4 bar, but possibly even as high as 10 bar.

In use the button 21 will be pressed to force the piston 56 a short distance downwardly in the barrel portion 24, after which the gas released from the reservoir 11 will enter the barrel portion 24 behind the piston 56 and force the piston to stroke down within the chamber 25 until the pressure between the piston and capsule 28 is sufficient to burst the capsule diaphragm. In this example it is intended that the barrel portion 24 will be separated from the barrel portion 10 for disposal together with the piston 56.

Figure 6:
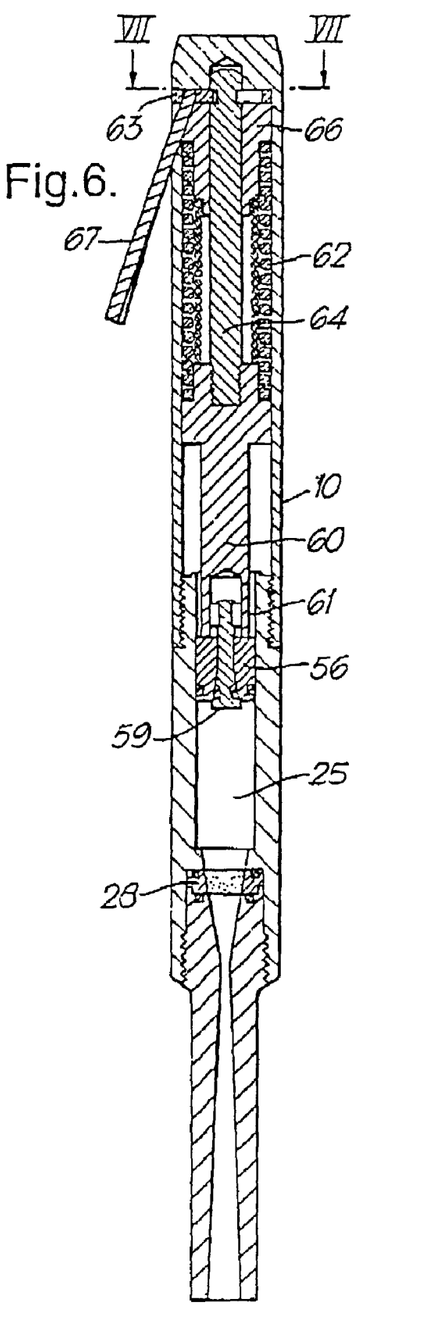
Figure 7:
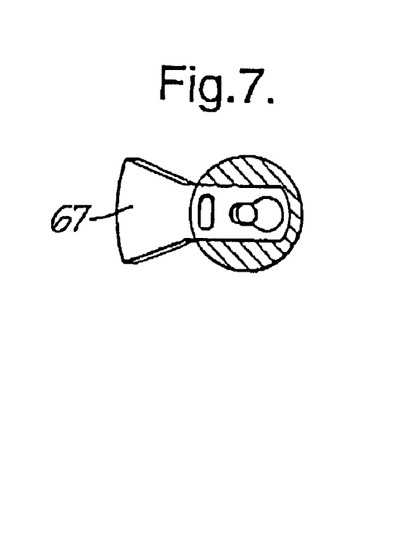
FIG. 7 is a section taken on the line VII-VII in FIG. 6; and,
FIG. 8 is an axial section through a capsule used in the illustrated syringes.

The syringe shown in FIGS. 6 and 7 has disposable parts which are similar to those of the syringe shown in FIG. 5, except that the piston 56 is of a slightly different shape and contains a poppet valve 59 through which the chamber 25 can be precharged with gas under a superatmospheric pressure. In this case the upper barrel portion 10 contains a sliding plunger 60 having an annular leading end 61 which is arranged to engage the piston 56 around the poppet valve 59. The plunger 60 is initially held retracted, against the action of a pair of parallel helically coiled compression springs 62 by Leans of a keyhole slotted plate 63 which is laterally slidable in the upper end of the barrel portion 10, and engages a complementary annular groove in the upper end of a stem 64 which screws into an enlargement 65 at the upper end of the plunger, and effectively forms an extension of the plunger. The springs 62 act between the enlargement 65 and a shoulder on an insert 66 within the barrel portion. The slotted plate 63 is laterally movable by means of a finger lever 67.

Initially with the plunger 60 cocked and retracted, and with the piston 56 at the upper end of the chamber 25, a spacer at the lower end of the syringe is applied, as previously described, to a patient's skin. Depression of the lever 67 releases the stem 64 and plunger 60, which drives the piston 56 forwardly until the pressure in the chamber 25 is sufficient to burst the diaphragms of the capsule 28.

In each of the examples, the geometry of the passageway through the nozzle 26 and of the spacer shroud 38 are significant and the following are typical for a nominal Mach 2 velocity nozzle. The convergent portion 35 is 10 mm long and converges from a diameter of 6 mm to a diameter at the throat 36 of 1.5 mm. The divergent portion 37 is 50mm long and the diameters at 5 mm increments from the throat 36 downstream to the outlet end of the nozzle are 1.74, 1.95, 2.03, 2.10, 2.16, 2.19, 2.20, 2.21, 2.22 and 2.23 mm respectively. The spacer shroud 38 has an axial length of 30 mm and diverges from an upstream diameter of 12 mm to 30 mm.

The examples shown in FIGS. 5 to 7 may be modified for laboratory use by providing in the wall of the barrel portion 24 an inlet port connected to a source of e.g. helium via which the chamber 25 can intermittently be pumped up to the initial pressure of 2-4 bar. In this case, it may not be necessary for the lower parts to be disposable, nor to be provided preassembled. Thus the barrel portion 10 may be of rigid construction and held in a secure position. The particulate material may be provided between the diaphrages 33, 34, of a sealed unit 28 between portion 10 and nozzle 26. However, in the laboratory, it may be sufficient for there to be a single membrane on to which the particulate material is dosed through the top of the barrel portion 10, prior to fitting of the piston 56 into the top of the portion 10, and the raising of the pressure within the cylinder via the inlet port. Thereafter the driving gas is applied to depress the piston 56.

The invention claimed is:

1. A needleless syringe comprising:
   an elongate tubular nozzle;
   a rupturable membrane initially closing a passage through the nozzle adjacent an upstream end of the nozzle;
   particles located adjacent to the membrane and between two rupturable diaphragms; and
   energizing means for applying to an upstream side of the membrane a gaseous pressure sufficient to burst the membrane and to produce through the nozzle a gas flow in which the particles are entrained.

2. A syringe according to claim 1, wherein the energizing means comprises:
   a chamber upstream of the membrane; and
   means for a controlled increase of gaseous pressure in the chamber.

3. A syringe according to claim 2, wherein the means for increasing the pressure in the chamber comprises a source of compressed gas connected to the chamber.

4. A syringe according to claim 3, wherein the syringe is self-contained and portable, and wherein the syringe comprises a reservoir of compressed gas.

5. A syringe according to any one of the preceding claims, wherein the gas applied to the upstream side of the membrane to burst the membrane is lighter than air.

6. A syringe according to any one of claims 1 to 4, wherein the particles are of a powdered therapeutic agent.

7. A syringe according to claim 6, wherein the syringe comprises at least three diaphragms, wherein the diaphragms define separate spaces for containment of different types of particles.

8. A syringe according to claim 6, wherein the two rupturable diaphragms extend across an interior of the nozzle.

9. A syringe according to claim 1, wherein the rupturable membrane is provided by the rupturable diaphragms.

10. A syringe according to any one of claims 1 to 4 or 9, wherein the diaphragms are sealed together around edges thereof to form a common sachet or capsule containing the particles.

11. A syringe according to claim 10, wherein at least one of the two diaphragms is dimpled away from the other to provide separation sufficient to locate the majority of the particles radially inwardly of the diaphragm edges.

12. A syringe according to claim 1, wherein, downstream of the membrane, an interior of the nozzle contains a gas that is less dense than air, and wherein the gas is contained by a readily removable seal at a downstream end of the nozzle.

13. A syringe according to claim 12, wherein the seal is a removable plug or cap.

14. A syringe according to claim 12, wherein the seal is a peelable foil.

15. A syringe according to any one of claims 12 to 14, wherein the gas contained within the nozzle is helium.

16. A syringe according to any one of claims 1 to 4, 9, or 12 to 14, wherein the nozzle is convergent/divergent downstream of the membrane.

17. A syringe according to claim 1, wherein a spacer is provided at a downstream end of the nozzle to provide a positive spacing of the nozzle from a target.

18. A syringe according to claim 17, wherein the spacing is up to 35 mm.

19. A syringe according to claim 17 or claim 18, wherein the spacer is a tubular shroud sufficiently large and shaped so that it is configured to allow a jet of gas-entrained particles leaving the nozzle outlet, in use, to expand to a cross section at least five times the area of the outlet at a position level with the downstream end of the shroud.

20. A syringe according to any one of claims 17 or 18, wherein the spacer is an imperforate tubular shroud, wherein a silencer is positioned in an annular space within a barrel surrounding the tubular nozzle, and wherein the silencer is configured to receive a shock wave reflected from the target back through the spacer shroud.

21. A syringe according to any one of claims 1 to 4, 9, 12 to 14, 17, or 18, wherein the syringe is readily separable into a disposable downstream part and an upstream part, wherein the downstream disposable part comprises at least the nozzle, membrane and particles, and wherein the upstream part comprises at least part of the energizing means.

22. A sterile package containing the downstream disposable part of the syringe according to claim 21.

23. A syringe according to claim 17, wherein the spacing is between 5-15 mm.

24. A syringe according to claim 1, wherein the gas flow produced in which the particles are entrained is supersonic.

25. A syringe according to claim 1, wherein the syringe, on activation, is configured to deliver the particles through the nozzle at a velocity in the range of between about 200 m/s and about 2,500 m/s, wherein the particles have a size predominantly in the range of between about 0.1 µm and about 250 µm, and wherein a density of the particles is predominantly in the range of between about 0.1 g/cm$^3$ and about 25 g/cm$^3$.

26. A syringe according to claim 1, wherein the particles have a size and density such that the syringe, on activation, is configured to deliver the particles to a transdermal penetration depth of between about 100 µm and about 500 µm.

27. A syringe according to claim 1, wherein the particles are coated with DNA.

28. A syringe according to claim 1, wherein the particles are dry.

29. A syringe according to claim 1, wherein the particles have a size predominantly in a range of 0.1 to 10 µm.

30. A syringe according to claim 1, wherein the particles comprise dense carrier particles.

31. A syringe according to claim 30, wherein the dense carrier particles are gold.

32. A syringe according to claim 30, wherein the dense carrier particles are tungsten.

33. A syringe according to claim 30, wherein the dense carrier particles are coated with genetic material.

34. A syringe according to claim 30, wherein the dense carrier particles are coated with DNA.

35. A syringe according to claim 1, wherein said particles have a density of an order of 20 g/cm$^3$.

36. A needleless syringe comprising:
a nozzle;
particles provided between two rupturable diaphragms; and
energizing means,
wherein, on activation, the syringe is configured to entrain the particles in a gas flow and deliver the particles through the nozzle at a velocity of at least 200 m/s, and wherein the particles have a size predominantly in the range 0.1 to 250 µm and a density in the range of 0.1 to 25 g/cm$^3$.

37. A syringe according to claim 36, wherein the particles are of a powdered therapeutic agent.

38. A syringe according to claim 37, wherein the agent has substantially no inert carrier or diluent by volume.

39. A syringe according to claim 36 or claim 38, wherein the velocity range is between 500 m/s and 1,500 m/s and/or the size range is between 0.1 µm and 50 µm and/or the density range is between 2.0 g/cm$^3$ and 25 g/cm$^3$.

40. A syringe according to claim 39, wherein the velocity range is between 750 m/s and 1,000 m/s and/or the size range is between 0.1 µm and 10 µm; and/or the density is substantially 19.3 g/cm$^3$.

41. The needleless syringe according to claim 36 wherein, the syringe is configured to deliver the particles through the nozzle at a velocity of in the range of between 200 m/s and 2,500 m/s.

42. A needleless syringe comprising:
a nozzle;
particles; and
energizing means,
wherein, on activation, the syringe is configured to entrain the particles in a gas flow and deliver the particles with a momentum density of between 2 kg/s/m and 10 kg/s/m.

43. A syringe according to claim 42, wherein, on activation, the syringe is configured to deliver the particles with a momentum density of between 4 kg/s/m and 7 kg/s/m.

* * * * *